United States Patent [19]

Samain

[11] Patent Number: 5,833,966
[45] Date of Patent: Nov. 10, 1998

[54] HYDROGEN PEROXIDE-BASED COMPOSITIONS USED AS FIXERS FOR PERMANENT-WAVING/STRAIGHTENING

[75] Inventor: Henri Samain, Bievres, France

[73] Assignee: L'Oreal, Paris, France

[21] Appl. No.: 730,059

[22] Filed: Oct. 15, 1996

Related U.S. Application Data

[63] Continuation of Ser. No. 281,201, Jul. 27, 1994, abandoned.

[30] Foreign Application Priority Data

Jul. 28, 1993 [FR] France ................................. 93 09287

[51] Int. Cl.$^6$ .............................. A61K 7/07; A61K 7/09
[52] U.S. Cl. ........................................ 424/70.2; 424/70.5
[58] Field of Search .................................. 424/70.2, 70.5

[56] References Cited

U.S. PATENT DOCUMENTS

| | | |
|---|---|---|
| 2,350,178 | 5/1944 | Martin . |
| 3,628,544 | 12/1971 | Kalopissis et al. . |
| 3,768,490 | 10/1973 | Kalopissis et al. . |
| 4,313,933 | 2/1982 | Yamazaki . |
| 4,323,360 | 4/1982 | Bugaut et al. . |
| 4,324,553 | 4/1982 | Bugaut et al. . |
| 4,330,292 | 5/1982 | Bugaut et al. . |
| 4,349,537 | 9/1982 | Forbriger, Jr. . |
| 4,366,827 | 1/1983 | Madrange et al. . |
| 4,533,714 | 8/1985 | Sebag et al. . |
| 4,749,732 | 6/1988 | Kohl et al. . |
| 4,832,948 | 5/1989 | Kondo . |
| 4,834,767 | 5/1989 | Helioff et al. . |
| 4,880,618 | 11/1989 | Grollier et al. . |
| 4,956,175 | 9/1990 | Maignan et al. . |
| 4,996,059 | 2/1991 | Grollier et al. . |
| 5,080,890 | 1/1992 | Ueno . |
| 5,208,014 | 5/1993 | Dubief et al. . |

FOREIGN PATENT DOCUMENTS

| | | |
|---|---|---|
| 845277 | 6/1970 | Canada . |
| 295780 A1 | 12/1988 | European Pat. Off. . |
| 354835 A1 | 2/1990 | European Pat. Off. . |
| 368763 A1 | 5/1990 | European Pat. Off. . |
| 394930A1 | 10/1990 | European Pat. Off. . |
| 432000 A1 | 6/1991 | European Pat. Off. . |
| 512879 A2 | 11/1992 | European Pat. Off. . |
| 514282 A1 | 11/1992 | European Pat. Off. . |
| 1530369 | 5/1968 | France . |
| 2472382 | 7/1981 | France . |
| 2495931 | 6/1982 | France . |
| 2535730 | 11/1984 | France . |
| 2598613 | 11/1987 | France . |
| 2679448 | 1/1993 | France . |
| 91 03 513.9 | 7/1992 | Germany . |
| 1009919 | 1/1989 | Japan . |
| 1163298A2 | 6/1989 | Japan . |
| 2197352 | 5/1988 | United Kingdom . |

OTHER PUBLICATIONS

Zviak, *The Science of Hair Care,* 1986, pp. 221–224.

*Primary Examiner*—Sally Gardner-Lane
*Attorney, Agent, or Firm*—Finnegan, Henderson, Farabow, Garrett, & Dunner, L.L.P.

[57] ABSTRACT

Hydrogen peroxide-based compositions for the manufacture of, or use as fixers for, permanent-waving/straightening. The compositions comprise hydrogen peroxide and at least one carboxylic acid and/or a salt thereof, for example, citric acid, as well as at least one alkalinizing amino compound, for example, aqueous ammonia. Processes for the permanent-reshaping and/or shape-stabilizing of keratinous materials, especially hair, are also disclosed. The compositions according to the invention make it possible to overcome the drawbacks relating to softness, sensitization to dyeing, etc., associated in the prior art particularly with repeated application to the hair of permanent-waving/straightening operations, in particular those involving the use of carbonate.

8 Claims, No Drawings

HYDROGEN PEROXIDE-BASED COMPOSITIONS USED AS FIXERS FOR PERMANENT-WAVING/STRAIGHTENING

This is a continuation of application Ser. No. 08/281,201, filed Jul. 27, 1994 now abandoned.

The present invention relates to the use of so-called oxidizing compositions based on hydrogen peroxide in processes for the permanent-shape-stabilizing and/or -reshaping of keratinous materials, especially hair.

The most common technique used for obtaining a permanent-reshaping of hair is known to consist, in a first stage, of carrying out the opening of the disulphide bonds —s—s— of keratin (cystine) using a composition containing a reducing agent (i.e., reduction step), and then, preferably after rinsing the hair thus treated, in reconstituting the disulphide bonds in a second stage by applying, to the hair previously placed under tension (created by curlers and the like), an oxidizing composition (i.e., an oxidation step, also termed a fixing step) so as to provide the desired shape to the hair. This technique makes it possible to carry out with equal success both the waving of hair or the uncurling or straightening of hair. The new shape imposed upon the hair by a chemical treatment such as the above is eminently durable over time and withstands, in particular, the action of water or shampoo washes, as opposed to the traditionally simple techniques for the temporary reshaping of hair, such as setting.

The reducing compositions which may be used for carrying out the first step of a permanent-waving/straightening operation generally contain, as reducing agents, sulphites or, preferably, thiols. Among the thiols, those commonly used are cysteine and its various derivatives, cysteamine and its derivatives, thiolactic acid, thioglycolic acid as well as its esters, in particular glyceryl monothioglycolate, and thioglycerol.

To carry out the above-mentioned oxidation or fixing step, it is preferred to employ cosmetically acceptable compositions based on hydrogen peroxide.

One of the problems with the permanent-waving/straightening techniques known to date is that their repeated application on the hair eventually induces a considerable modification of the behavior of the hair, particularly with respect to the subsequent ability of the hair to be dyed correctly. It has been observed that, on hair which has undergone a few permanent-waving/straightening operations (on the order of three at most), the dyeing will be much more pronounced than that obtained on the same hair had it not been subjected to permanent-waving/straightening operations. A problem is thus created in those cases where the dyeing operation is performed on a head of hair which has previously been subjected to permanent-waving/straightening but which has also grown since the hair was treated. Poor matching between the hair previously subjected to permanent-waving/straightening and the regrowth hair, not subjected to permanent-waving/straightening, is experienced. It has been observed, moreover, that dyeing becomes very difficult, or even impossible, if the hair to be dyed has previously undergone a large number of permanent-waving/straightening operations, in particular, more than five operations.

Another problem lies in the fact that, for various reasons, it is generally necessary to buffer the pH of the reducing composition by adding certain additives, particularly carbonate products such as, for example, carbonic acid or carbon dioxide, alkali metal or ammonium carbonates or bicarbonates or organic carbonates such as, in particular, guanidine carbonate.

It unfortunately proves to be the case that the repeated application of permanent-shape-stabilizing/reshaping operations using carbonate-containing reducing compositions combined with hydrogen peroxide-based oxidizing compositions eventually brings about a gradual and marked degradation of the quality of the individual hair, particularly with respect to the softness of the fibers, which tend to become increasingly rough.

The object of the present invention is, in particular, to solve the above problems.

It has been found by the Applicant that the use of certain oxidizing compositions, based on hydrogen peroxide, may provide successful remedies to the various drawbacks inherently associated with repeated application to the hair of reducing compositions, particularly those containing carbonate, and of oxygenated oxidizing compositions.

Hydrogen peroxide-based compositions of the present invention for the permanent reshaping and/or shape-stabilizing of keratinous materials (hereinafter designated "oxidizing" compositions for the purposes of this application) comprise hydrogen peroxide and (i) at least one carboxylic acid and/or one of its associated salts, and (ii) at least one alkalinizing amino compound.

The oxidizing compositions of the invention are utilized as, or for the manufacture of, fixers for permanent-waving/straightening.

The present invention is also directed to a multi-compartment device or kit which comprises a reducing composition, particularly one containing carbonate, in a first compartment, and an oxidizing composition according to the invention in a second compartment. The multi-compartment device or kit is produced for the purpose, in particular, of carrying out a treatment process for the permanent-reshaping and/or shape-stabilizing of keratinous materials, especially hair.

The present invention is further directed to a treatment process for the reshaping and/or shape-stabilizing of keratinous materials, especially hair. The treatment process of the invention comprises, in a first step, reducing the disulphide bonds of keratin by application of a reducing composition, particularly one containing carbonate, and in a second step, reforming said disulphide bonds by application of a hydrogen peroxide-based oxidizing composition. Said treatment process further comprises utilization of an oxidizing composition according to the invention or a kit according to the invention.

Other features, aspects, subjects and advantages of the invention will become more apparent upon a reading of the detailed description which follows, as well as a reading of the various specific, but in no way limiting, examples designed to illustrate the invention.

Although the account which follows is essentially structured around the specific case of the treatment of hair, it may be noted here that the present invention is in no way limited thereto. On the contrary, the present invention is applicable to any keratinous material in general, in particular eyelashes, moustaches, bristles, wool and the like.

Representative carboxylic acids which may be used in the compositions according to the invention are lactic, tartaric, acetic, glycolic and citric acids. Carboxylic acids are thus understood to denote and cover, in particular, mono-carboxylic acids, polycarboxylic acids and (poly)hydroxy (poly)carboxylic acids, which may naturally be taken alone or in combination.

Generally speaking, any compound possessing at least one carboxyl function, i.e.,

and which is capable of lowering (in its acid region) the pH of a hydrogen peroxide solution is capable of being used in the present invention. Preferably, acids which are cosmetically compatible with the hair, skin and/or scalp will be selected.

According to a particularly preferred embodiment of the present invention, the acid employed is citric acid.

As stated above, it should be noted that the carboxylic acids used according to the invention can be present in the final compositions, partially or totally, in the form of one of their associated salts; this presence and the extent thereof depends particularly on the final pH imposed on the final composition.

Representative alkalinizing amino compounds which may be used in the oxidizing compositions according to the invention include aqueous ammonia and primary, secondary or tertiary (poly)amines such as, for example, monoethanolamine, diethanolamine, triethanolamine, isopropanolamine and 1,3-propanediamine. In general, it is possible to use any diamine corresponding to the following formula:

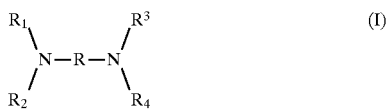

in which R is a propylene residue optionally substituted with a hydroxyl group or a $C_1$–$C_4$ alkyl radical; and $R_1$, $R_2$, $R_3$ and $R_4$ represent, simultaneously or independently of one another, hydrogen or a $C_1$–$C_4$ alkyl or hydroxyalkyl radical. Exemplary diamines are described in EP-A-512,879, the disclosure of which is specifically incorporated by reference herein.

Preferably, aqueous ammonia or monoethanolamine is employed.

All of the alkalinizing amino compounds mentioned above may be used alone or in combination.

Alkalinizing is understood here to denote the fact that the amino compound is capable of raising the natural pH of water (pH 7) to a value above 7.

According to the invention, the oxidizing compositions may be prepared either by first adding the carboxylic acid (which can then take the form of a liquid or solid) to a hydrogen peroxide solution and then adding the amino compound (solid or liquid) to the resulting mixture, or vice versa. Simultaneous introduction of the acid and the amino compound to the hydrogen peroxide solution is also possible.

In the specific case where the compositions according to the invention are intended for use as fixing agents for permanent-waving/straightening, the compositions preferably possess, furthermore, at least one of the following additional features:

the concentration of carboxylic acid(s) and/or of their associated salts therein is between 0.1N and 2N, and still more preferably between 0.2N and 1N;

the concentration of amino compound(s) therein is adjusted so that the final pH of the composition is between 2.8 and 6, and still more preferably between 4 and 5.5;

the hydrogen peroxide concentration varies from 1 to 20 volumes, i.e., from 0.3% by weight to 6% by weight of the composition, and still more preferably ranges from 1 to 10 volumes, i.e., from 0.3% by weight to 3% by weight of the composition;

the composition contains traditional and common cosmetically acceptable adjuvants; said adjuvants being, for example, chosen from nonionic, anionic, cationic or amphoteric type surfactants, treatment agents, active ingredients, agents for combatting hair loss, antidandruff agents, thickeners, suspending agents, sequestering agents, opacifying agents, colorants, sunscreen agents, perfumes and preservatives, alone or in combination, some of which additives will, moreover, be referred to in slightly more detail in the account which follows relating to the reducing compositions, particularly those containing carbonate, capable of being used in the process of the present invention and/or the kit according to the present invention, and in which compositions these same additives may traditionally be found; and the composition takes the form of a lotion, thickened or otherwise, a milk, a cream or gel, or any other suitable form.

Most generally speaking, the reducing compositions, which are capable of being used either in the production of a kit according to the invention or for carrying out the first step of the permanent-waving/straightening operation of a process according to the invention, can consist of any composition already known per se as a reducing composition. In particular, the reducing compositions can contain, as reducing agents, sulphites and/or bisulphites (in particular alkali metal, alkaline-earth metal or ammonium sulphites and/or bisulphites) or, preferably, thiols. Among the thiols, those most commonly used are cysteine and its various derivatives (in particular N-acetyl-cysteine), cysteamine and its various derivatives (in particular its $C_1$–$C_4$ acyl derivatives such as N-acetylcysteamine or N-propionylcysteamine), thiolactic acid and its esters (in particular glyceryl monothio-lactate), thioglycolic acid as well as its esters, in particular glyceryl or glycol monothioglycolate, and thioglycerol. The following reducing agents may also be mentioned: sugar N-mercaptoalkylamides such as N-(2-mercaptoethyl) gluconamide, β-mercaptopropionic acid and its derivatives, thiomalic acid, pantetheine, the N-(mercaptoalkyl)-ω-hydroxyalkylamides described in Patent Application EP-A-354,835, the disclosure of which is specifically incorporated by reference herein, and the N-mono- or N,N-di-alkyl-4-mercaptobutyramides described in Patent Application EP-A-368,763, the disclosure of which is specifically incorporated by reference herein, the aminomercaptoalkylamides described in Patent Application EP-A-432,000, the disclosure of which is specifically incorporated by reference herein, and the alkylaminomercaptoalkylamides described in Patent Application EP-A-514,282, the disclosure of which is specifically incorporated by reference herein, and the mixture of 2-hydroxy-propyl thioglycolate (2/3) and 2-hydroxy-1-methylethyl thioglycolate (67/33) described in Patent Application FR-A-2,679,448, the disclosure of which is specifically incorporated by reference herein.

As already stressed above, these reducing agents are generally employed in cosmetically acceptable compositions, which are, moreover, already well known per se in the existing prior art of curling formulations designed to carry out the first step (reduction) of a permanent-waving operation. Thus, representative common and traditional additives which are capable of being used, alone or in combination, in such cosmetic compositions containing reducing agents include nonionic, anionic, cationic or amphoteric type surfactants, and among these, alkyl sulphates, alkylbenzenesulphonates, alkyl ether sulphates, alkylsulphonates, quaternary ammonium salts, alkylbetaines, oxyethylenated alkylphenols, fatty acid alkanolamides and oxyethylenated fatty acid esters are preferred, as well as other nonionic surfactants of the hydroxypropyl ether type.

When the reducing composition contains at least one surfactant, the surfactant is generally present at a maximum concentration of 30% by weight, and preferably ranging from 0.5 to 10% by weight, relative to the total weight of the reducing composition.

For the purpose of improving the cosmetic properties of the hair, or alternatively, for the purpose of lessening or preventing the hair's degradation, the reducing composition can also contain a treatment agent of cationic, anionic, nonionic or amphoteric nature.

Among particularly preferred treatment agents, those described in French Patent Applications Nos. 2,598,613 and 2,470,596, the disclosures of which are specifically incorporated by reference herein, may be mentioned. It is also possible to use as treatment agents volatile or non-volatile, linear or cyclic silicones and mixtures thereof, polydimethylsiloxanes, quaternized polyorgano-siloxanes, such as those described in French Patent Application No. 2,535,730, the disclosure of which is specifically incorporated by reference herein, polyorganosiloxanes containing aminoalkyl groups modified by alkoxycarbonylalkyl groups, such as those described in U.S. Pat. No. 4,749,732, the disclosure of which is specifically incorporated by reference herein, polyorganosiloxanes, such as the polydimethylsiloxane/polyoxyalkyl copolymer of the dimethicone copolyol type, a polydimethylsiloxane containing terminal stearoxy groups (stearoxy dimethicone), a polydimethylsiloxane/dialkylammonium acetate copolymer or a polydimethyl-siloxane/polyalkylbetaine copolymer, which are described in British Patent Application No. 2,197,352, the disclosure of which is specifically incorporated by reference herein, and poly-siloxanes organo-modified by mercapto or mercapto alkyl groups, such as those described in French Patent No. 1,530,369 and in European Patent Application No. 295,780, the disclosures of which are specifically incorporated by reference herein, as well as silanes such as stearoxytrimethylsilane.

The reducing composition can also contain other treatment ingredients such as cationic polymers, such as those used in the compositions of French Patents Nos. 79/32078 (FR-A-2,472,382) and 80/26421 (FR-A-2,495,931), the disclosures of which are specifically incorporated by reference herein, or alternatively cationic polymers of the ionene type such as those used in the compositions of Luxemburg Patent No. 83703, the disclosure of which is specifically incorporated by reference herein, basic amino acids (such as lysine, arginine) or acidic amino acids (such as glutamic acid, aspartic acid), peptides and their derivatives, protein hydrolysates, waxes, swelling and penetrating agents or agents enabling the efficacy of the reducing agent to be enhanced, such as $SiO_2$PDMS (polydimethylsiloxane) mixture, dimethylisosorbitol, urea and its derivatives, pyrrolidone, N-alkylpyrrolidones, thiamorpholinone, alkylene glycol or dialkylene glycol alkyl ethers, such as, for example, propylene glycol monomethyl ether, dipropylene glycol monomethyl ether, ethylene glycol monoethyl ether and diethylene glycol monoethyl ether, $C_3$–$C_6$ alkanediols such as, for example, 1,2-propanediol and 1,2-butanediol, and 2-imidazolidinone, as well as other compounds such as fatty alcohols, lanolin derivatives, active ingredients such as pantothenic acid, agents for combating hair loss, anti-dandruff agents, thickeners, suspending agents, sequestering agents, opacifying agents, colorants and sunscreen agents, as well as perfumes and preservatives.

In permanent-waving/straightening reducing compositions, the reducing agents, such as those mentioned above, are generally present at a concentration which can range from 1 to 30% by weight, and preferably from 5 to 20% by weight, relative to the total weight of the reducing composition.

The reducing composition can take the form of a lotion, thickened or otherwise, a cream or a gel, or any other suitable form.

The reducing composition can also be exothermic, that is to say it causes some degree of warming up on application to the hair, which can impart a pleasant sensation to the person undergoing a permanent-waving or uncurling operation.

The reducing composition can also contain a solvent such as, for example, ethanol, propanol or isopropanol, or alternatively glycerol, at a maximum concentration of 20% relative to the total weight of the composition.

The vehicle of the compositions is preferably water or an aqueous-alcoholic solution of a lower alcohol such as ethanol, isopropanol or butanol.

When the compositions are designed for an operation of uncurling or straightening hair, the reducing composition is preferably in the form of a thickened cream so as to maintain the hair as stiff as possible. These creams are produced, in the form of "heavy" emulsions, for example, based on glyceryl stearate, glycol stearate, self-emulsifying waxes, fatty alcohols, and the like.

It is also possible to use liquids or gels containing thickening agents such as vinylcarboxylic polymers or copolymers which "stick" the hair and maintain it in the smooth position during the exposure time.

Lastly, the reducing compositions can also contain at least one disulphide which is known for its use in a reducing composition for self-neutralizing permanent-waving/straightening.

Among such known disulphides, dithioglycolic acid, dithioglycerol, cystamine, N,N'-diacetylcystamine, cystine, pantethine and the disulphides of the N-(mercaptoalkyl)-ω-hydroxyalkylamides described in European Patent Application EP 354,835, the disclosure of which is specifically incorporated by reference herein, the disulphides of the N-mono- or N,N-di-alkyl-4-mercaptobutyramides described in Patent Application EP 368,763, the disclosure of which is specifically incorporated by reference herein, the disulphides of the aminomercaptoalkylamides described in Patent Application EP 432,000, the disclosure of which is specifically incorporated by reference herein, and the disulphides of the alkylaminomercaptoalkylamides described in Patent Application EP 514,282, the disclosure of which is specifically incorporated by reference herein, are preferred. These disulphides are generally present in a mole ratio of 0.5:1 to 2.5:1, and preferably 1:1 to 2:1, relative to the reducing agent (see U.S. Pat. No. 3,768,490, the disclosure of which is specifically incorporated by reference herein).

The pH values of the reducing compositions may be adjusted conventionally by adding either (1) alkalinizing agents such as, for example, aqueous ammonia, monoethanolamine, diethanolamine, triethanolamine, isopropanolamine, 1,3-propanediamine, an alkali metal or ammonium carbonate or bicarbonate, an organic carbonate such as guanidine carbonate (carbonate-containing reducing compositions) or alternatively an alkali metal hydroxide, it being possible for all these compounds naturally to be taken alone or in combination, or (2) acidifying agents such as, for example, hydrochloric acid, acetic acid, lactic acid or boric acid.

A process of the present invention for the permanent reshaping and/or shape-stabilizing of keratinous materials, especially hair, comprises the following preferred steps:

(i) applying a reducing composition, in particular that defined above, and particularly one containing carbonate, to the keratinous material to be treated, and placing the keratinous material under mechanical tension by means (such as, for example, rollers, curlers and the like) which may be deployed before, during or after applying said reducing composition, (ii) rinsing the keratinous material, (iii) applying an oxidizing composition according to the invention to the keratinous material, (iv) separating the treated keratinous material from the tension means (rollers and the like) used in step (i), (v) rinsing the keratinous material.

According to the first step of the process, (step (i)), the compositions containing the reducing agent or agents, as mentioned above, are applied to the hair to be treated, which will preferably have been previously wetted.

This application of the reducing composition to the hair may be carried out before, during or after the customary step of placing the hair under tension in a shape which corresponds to the desired final shape of the hair (curls for example). It is possible for the step of placing the hair under tension to be carried out by any suitable means, in particular mechanical, known per se for maintaining hair under tension, such as, for example, rollers, curlers and the like (roller diameter: generally from 4 to 20 mm).

Before proceeding to the first rinsing step, it is appropriate, in a traditional manner, to leave the hair to which the reducing composition has been applied undisturbed for a few minutes, generally from 2 to 30 minutes and preferably from 5 to 20 minutes, so as to allow due time for the reducing agent to act properly on the hair. This waiting phase is generally performed by allowing the treated hair to remain undisturbed while freely exposing the treated hair to the air (room temperature). A waiting phase performed at higher temperatures is not ruled out, but rather is considered suitable (salon hair drier, infrared ray emitter or any other standard heating apparatus). During the waiting phase, care is taken so that the hair does not dry completely. The hair thus remains wet until the next step is carried out (to this end, possible use can be made of standard bonnets and/or protections gels, for example).

In the second step of the process (step (ii)), the hair treated with the reducing composition is rinsed, preferably carefully, generally with water.

Then, in a third step (step (iii)), an oxidizing composition according to the invention is applied to the rinsed hair for the purpose of fixing the new shape imposed on the hair. As in the case of the application of the reducing composition, the hair to which the oxidizing composition has been applied is then, in a traditional manner, left in a waiting phase which may last for a few minutes, generally from 3 to 20 minutes and preferably from 5 to 15 minutes.

In the fourth step of the process (step (iv)), the mechanical means which were used (standard rollers, curlers and the like) to maintain the hair under tension and in the desired shape throughout the treatment process are removed from the hair.

In the final step of the process, (step (v)), the hair is rinsed carefully and copiously with water. After drying, (naturally, by exposure freely to the air, or by means of a standard heating apparatus), a head of hair which possesses, for example, attractive curls which are permanent (in particular, resistant to water) may be ultimately obtained.

Even when the process of the present invention is repeated several times on the same head of hair, and even when reducing compositions of the carbonate-containing type are used, the process of the present invention always results in hair which possesses, on the one hand, good softness, close to the original softness, and, on the other hand, very correct behavior upon dyeing.

Specific examples illustrating the invention will now be provided. For the purpose of obtaining a significant comparison, for any given example, the same initial hair (before treatment) was used to perform the test according to the invention and the comparative test. However, the initial hair was different for each example (Example 1: strongly bleached hair; Example 2: natural brown hair; Example 3: natural brown hair; Example 4: bleached hair; Example 5: natural grey European hair).

The carbonate-containing reducing composition consistently used to perform Examples 1 to 4 possessed the following features:

| thioglycolic acid | 9.1 g |
|---|---|
| mercaptopropionic acid | 2.2 g |
| ammonium carbonate | 7.3 g |
| aqueous ammonia in a quantity sufficient to obtain | pH 8.5 |
| a quantity sufficient of perfume | |
| a quantity sufficient of demineralized water to obtain | 100 g of composition |

The non-carbonate-containing reducing composition used to perform Example 5 possessed the following features:

| thioglycolic acid | 9.2 g |
|---|---|
| aqueous ammonia in a quantity sufficient to obtain | pH 8.5 |
| a quantity sufficient of demineralized water to obtain | 100 g of composition |

In addition, for all of the examples, the same procedure was used to perform each permanent-waving operation and was as follows: the reducing composition was applied to wet hair that had been wound around standard rollers, (roller diameter: 9 mm); a standard plastic bonnet was then placed over the hair and 15 min were allowed to elapse; the bonnet was then removed and the hair was rinsed copiously with water; the oxidizing composition was then applied to the hair and 10 min were allowed to elapse; the rollers were then removed; and the hair was then rinsed once again with water and then dried.

As used herein, 10 V or 10 volumes of hydrogen peroxide corresponds to 3% by weight.

EXAMPLE 1

Four successive permanent-waving operations were carried out according to the procedure provided above (shampooing plus drying under a standard salon drier between each waving). Each permanent-waving operation used an oxidizing composition according to the invention as a fixing composition. The oxidizing composition according to the invention had the following features:

| | |
|---|---|
| hydrogen peroxide in a quantity sufficient to obtain | 8 V |
| citric acid | 4 g |
| aqueous ammonia (20%) in a quantity sufficient to obtain | pH 4.5 |
| demineralized water in a quantity sufficient to obtain | 100 g of composition |

Following four successive permanent-wave operations, a lock of hair (no. 1) was thereby obtained.

By way of comparison, the above working protocol (four permanent-waving operations) was reproduced, but the comparative example employed the following fixing composition (not according to the invention):

| | |
|---|---|
| hydrogen peroxide in a quantity sufficient to obtain | 8 V |
| citric acid in a quantity sufficient to obtain | pH 4.5 |
| demineralized water in a quantity sufficient to obtain | 100 g of composition |

A lock of hair (no. 2) was thereby obtained.

It was found that lock no. 1 was much softer and less crumpled than lock no. 2.

A panel of 10 people judged these two locks on the criteria of softness, smoothing and crumpling (sensory appraisal test), and gave marks ranging from 0 to 5.0 corresponds to an unacceptable state, whereas 5 corresponds to an excellent result. Smoothing reflects the feel, and crumpling corresponds to the visual impression.

The mean scores were as follows:

| Criterion | Lock no. 1 | Lock no. 2 |
|---|---|---|
| Softness | 3.4 | 1.75 |
| Crumpling | 3.15 | 1.5 |
| Smoothing | 3.15 | 1.55 |

EXAMPLE 2

The procedure of Example 1 was reproduced, except that (i) the comparative oxidizing composition (not according to the invention) which was employed in this case had the following features:

| | |
|---|---|
| hydrogen peroxide in a quantity sufficient to obtain | 8 V |
| citric acid | 4 g |
| demineralized water in a quantity sufficient to obtain | 100 g of composition | and (ii) the permanent-waving operation was repeated only twice.

New locks of hair (lock no. 3, according to the invention; lock no. 4, comparative) were thereby obtained, for which the results of the judging panel (identical to that of Example 1) were as follows:

| Criterion | Lock no. 3 | Lock no. 4 |
|---|---|---|
| Softness | 3.6 | 2.9 |
| Crumpling | 4.3 | 2.5 |
| Smoothing | 3.85 | 2.85 |

EXAMPLE 3

The procedure of Example 1 was reproduced, except that the comparative oxidizing composition (not according to the invention) which was employed had the following features:

| | |
|---|---|
| hydrogen peroxide in a quantity sufficient to obtain | 8 V |
| citric acid | 4 g |
| sodium hydroxide in a quantity sufficient to obtain | pH 4.5 |
| demineralized water in a quantity sufficient to obtain | 100 g of composition |

Two new locks (lock no. 5, according to the invention; lock no. 6, comparative) were thereby obtained, which were scored by the judging panel as follows:

| Criterion | Lock no. 5 | Lock no. 6 |
|---|---|---|
| Softness | 3.75 | 3 |
| Crumpling | 3.9 | 1.65 |
| Smoothing | 3.65 | 2.45 |

EXAMPLE 4

Reproducing the procedure of Example 1, the same general softness, crumpling and smoothing results were obtained by employing the following oxidizing compositions according to the invention:

Composition A

| | |
|---|---|
| hydrogen peroxide (60% of active substance) | 4 g |
| citric acid | 2 g |
| aqueous ammonia in a quantity sufficient to obtain | pH 4.5 |
| demineralized water in a quantity sufficient to obtain | 100 g of composition |

Composition B

| | |
|---|---|
| hydrogen peroxide (60% of active substance) | 4.8 g |
| citric acid | 1.8 g |
| monoethanolamine in a quantity sufficient to obtain | pH 4.2 |
| demineralized water in a quantity sufficient to obtain | 100 g of composition |

Composition C

| | |
|---|---|
| hydrogen peroxide (60% of active substance) | 3.6 g |
| citric acid | 3.2 g |
| triethanolamine in a quantity sufficient to obtain | pH 4.8 |
| demineralized water in a quantity sufficient to obtain | 100 g of composition |

Composition D

| | |
|---|---|
| hydrogen peroxide (60% of active substance) | 4 g |

-continued

| | |
|---|---|
| citric acid | 3 g |
| 1,3-propanediamine in a quantity sufficient to obtain | pH 5 |
| demineralized water in a quantity sufficient to obtain | 100 g of composition |
| Composition E | |
| | |
| hydrogen peroxide (60% of active substance) | 4 g |
| lactic acid | 1.6 g |
| aqueous ammonia in a quantity sufficient to obtain | pH 4.5 |
| demineralized water in a quantity sufficient to obtain | 100 g of composition |
| Composition F | |
| | |
| hydrogen peroxide (60% of active substance) | 6 g |
| lactic acid | 2 g |
| monoethanolamine in a quantity sufficient to obtain | pH 4.2 |
| demineralized water in a quantity sufficient to obtain | 100 g of composition |
| Composition H | |
| | |
| hydrogen peroxide (60% of active substance) | 4 g |
| citric acid | 1 g |
| lactic acid | 1 g |
| aqueous ammonia in a quantity sufficient to obtain | pH 4.8 |
| demineralized water in a quantity sufficient to obtain | 100 g of composition |
| Composition I | |
| | |
| hydrogen peroxide (60% of active substance) | 4.5 g |
| glycolic acid | 1.5 g |
| aqueous ammonia in a quantity sufficient to obtain | pH 4.5 |
| demineralized water in a quantity sufficient to obtain | 100 g of composition |
| Composition J | |
| | |
| hydrogen peroxide (60% of active substance) | 2.8 g |
| glycolic acid | 2 g |
| monoethanolamine in a quantity sufficient to obtain | pH 4.5 |
| demineralized water in a quantity sufficient to obtain | 100 g of composition |
| Composition K | |
| | |
| hydrogen peroxide (60% of active substance) | 4 g |
| citric acid | 1.8 g |
| glycolic acid | 1 g |
| aqueous ammonia in a quantity sufficient to obtain | pH 4.5 |
| demineralized water in a quantity sufficient to obtain | 100 g of composition |
| Composition L | |
| | |
| hydrogen peroxide (60% of active substance) | 4 g |
| tartaric acid | 2.2 g |
| aqueous ammonia in a quantity sufficient to obtain | pH 4.5 |
| demineralized water in a quantity sufficient to obtain | 100 g of composition |
| Composition M | |
| | |
| hydrogen peroxide (60% of active substance) | 4 g |
| acetic acid | 1.6 g |
| monoethanolamine in a quantity sufficient to obtain | pH 4.5 |
| demineralized water in a quantity sufficient to obtain | 100 g of composition |

EXAMPLE 5

The object of this example was to show the advantage of the compositions according to the invention in the context of carrying out permanent-waving/straightening operations without involving the use of carbonate.

The same procedure as that provided above was followed: a lock of hair was subjected to repetitions (varying in number) of identical permanent-waving operations. These operations were performed systematically using the reducing composition not containing carbonate, the composition of which is provided at the beginning of the examples, but with an oxidizing composition which was either according to the invention (Formulation No. 1) or not according to the invention (Formulation No. 2), both of which are described below.

The lock of hair thereby obtained was then treated with a commercial dye (basic color blond, red tinge) in order to dye it.

The results of the dyeing were noted 30 min after application of the dye, by measuring the trichromaticity coordinates L, a and b of the hair (MINOLTA CHROMA METER 2002 calorimeter).

The results were collated in the table shown below.

The oxidizing formulations which were employed had the following features:

| | |
|---|---|
| Formulation no. 1 (invention) | |
| | |
| hydrogen peroxide (60% of active substance) | 4 g |
| citric acid | 2 g |
| aqueous ammonia in a quantity sufficient to obtain | pH 4.5 |
| demineralized water in a quantity sufficient to obtain | 100 g of composition |
| Formation no. 2 (comparative) | |
| | |
| hydrogen peroxide (60% of active substance) | 4.8 g |
| citric acid in a quantity sufficient to obtain | pH 3 |
| demineralized water in a quantity sufficient to obtain | 100 g of composition |

It was observed that the use of a fixer according to the invention (in this case citric acid+aqueous ammonia) made it possible to delay the phenomenon of sensitization of the hair fibers (lock no. 3), which phenomenon leads in the traditional case to an impossibility of dyeing the hair. The markedly higher parameter L in the case of lock no. 6 than in the case of lock no. 4 stemmed from the fact that lock no. 6 would no longer dye normally. This phenomenon was not observed when the locks were treated by permanent-waving operations which employed fixers according to the invention, since the dyeing results of locks nos. 1, 2 and 3, based solely on coordinate L, were very similar.

| Lock | Number of permanent-waving operations | Oxidizing formulation | Chromaticity coordinates | | |
|---|---|---|---|---|---|
| | | | L | a | b |
| 1 (inv) | 2 | 1 | 30.0 | 16.0 | 10.6 |
| 2 (inv) | 5 | 1 | 28.9 | 12.2 | 7.1 |
| 3 (inv) | 10 | 1 | 27.6 | 11.4 | 7.7 |
| 4 (comp) | 2 | 2 | 29.6 | 15.6 | 9.9 |

-continued

| Lock | Number of permanent-waving operations | Oxidizing formulation | Chromaticity coordinates | | |
|---|---|---|---|---|---|
| | | | L | a | b |
| 5 (comp) | 5 | 2 | 29.7 | 15.1 | 10.6 |
| 6 (comp) | 10 | 2 | 35.3 | 11.7 | 12.1 |

What is claimed is:

1. A method for improving a property of the hair during the fixative stage of a permanent waving/straightening of said hair; wherein said property is selected from the group consisting of softness, crumpling and smoothing said method comprising and oxidizing wherein said oxidizing comprises applying to said keratinous material a hydrogen peroxide-based composition comprising hydrogen peroxide and (i) at least one cosmetically acceptable carboxylic acid and/or a salt thereof, and (ii) at least one cosmetically acceptable alkalinizing amino compound, wherein the pH of said composition ranges from 2.8 to 6.0.

2. A multi-compartment kit which comprises in a first compartment, a reducing composition, and in a second compartment, a hydrogen peroxide-based composition comprising hydrogen peroxide and (i) at least one cosmetically acceptable carboxylic acid and/or a salt thereof, and (ii) at least one cosmetically acceptable alkalinizing amino compound, wherein said carboxylic acid is a lactic, tartaric, acetic, glycolic or citric acid, said alkalinizing amino compound is monoethanolamine, triethanolamine, isopropanolamine or 1,3-propanediamine, and wherein the pH of said composition ranges from 2.8 to 6.0.

3. A kit according to claim 2, wherein said reducing composition is a carbonate-containing reducing composition capable of and designed for carrying out the first step of a permanent-waving/straightening operation and wherein said hydrogen peroxide-based composition is capable of and designed for carrying out a subsequent step of said permanent-waving/straightening operation.

4. A process for improving a property of the hair during the fixative stage of a permanent reshaping and/or shape-stabilizing of said hair; wherein said property is selected from the group consisting of softness, crumpling and smoothing, which comprises in a first step, reducing the disulphide bonds of keratin by application to said keratinous material of a reducing composition, and in a subsequent step, re-forming said disulphide bonds by application to said keratinous material of a hydrogen peroxide-based oxidizing composition comprising hydrogen peroxide and (i) at least one cosmetically acceptable carboxylic acid and/or a salt thereof, and (ii) at least one cosmetically acceptable alkalinizing amino compound, wherein the pH of said composition ranges from 2.8 to 6.0.

5. A process according to claim 4, wherein said reducing composition is a carbonate-containing reducing composition.

6. A process according to claim 4, which comprises the following steps:

(i) applying said reducing composition to the keratinous material to be treated, and placing the keratinous material under mechanical tension before, during or after applying said reducing composition;

(ii) rinsing the treated keratinous material;

(iii) applying the oxidizing composition or fixer to the rinsed keratinous material;

(iv) separating the treated keratinous material from the tension means used in step (i); and (v) rinsing the separated keratinous material.

7. A method for the manufacture of a fixer for permanent-waving/straightening which comprises combining hydrogen peroxide and (i) at least one carboxylic acid and/or a salt thereof, and (ii) at least one alkalinizing amino compound to obtain a hydrogen peroxide-based fixer, wherein said carboxylic acid is a lactic, tartaric, acetic, glycolic or citric acid, said alkalinizing amino compound is monoethanolamine, triethanolamine, isopropanolamine or 1,3-propanediamine, and wherein the pH of said composition ranges from 2.8 or 6.0.

8. A hydrogen peroxide-based composition comprising hydrogen peroxide and (i) at least one cosmetically acceptable carboxylic acid and/or a salt thereof, and (ii) at least one cosmetically acceptable alkalinizing amino compound, wherein said carboxylic acid is a lactic, tartaric, acetic, glycolic or citric acid, said alkalinizing amino compound monoethanolamine, triethanolamine, isopropanolamine or 1,3-propanediamine, and wherein the pH of said composition ranges from 2.8 to 6.0.

* * * * *

UNITED STATES PATENT AND TRADEMARK OFFICE
CERTIFICATE OF CORRECTION

PATENT NO. : 5,833,966
DATED : November 10, 1998
INVENTOR(S) : Henri SAMAIN

It is certified that error appears in the above-identified patent and that said Letters Patent is hereby corrected as shown below:

<u>In the Claims</u>: Claim 1, col. 13, line 16, after "comprising" insert --reducing--.

Signed and Sealed this

Sixth Day of July, 1999

Attest:

Q. TODD DICKINSON

*Attesting Officer*     Acting Commissioner of Patents and Trademarks